United States Patent [19]

Zierdt

[11] 4,081,356

[45] Mar. 28, 1978

[54] FECALATOR, AN APPARATUS AND METHOD FOR CONCENTRATION OF PARASITE EGGS AND LARVAE

[75] Inventor: Willadene S. Zierdt, Rockville, Md.

[73] Assignee: The United States of America as represented by the Department of Health, Education and Welfare, Washington, D.C.

[21] Appl. No.: 726,218

[22] Filed: Sep. 24, 1976

[51] Int. Cl.² .............................................. B03B 7/00
[52] U.S. Cl. .......................................... 209/3; 209/17
[58] Field of Search ...................... 209/3, 17, 172, 173; 23/230 B, 292; 233/2, 26, 1 R; 210/65, 83, DIG. 24, 339, 359; 259/72

[56] References Cited

U.S. PATENT DOCUMENTS

| 1,775,109 | 9/1930 | Picker | 233/26 |
|---|---|---|---|
| 3,087,707 | 4/1963 | Moonan | 259/72 X |
| 3,300,051 | 1/1967 | Mitchell | 210/339 |
| 3,819,045 | 6/1974 | Breenwald | 209/17 |
| 3,942,717 | 3/1976 | Robison | 210/DIG. 24 |

OTHER PUBLICATIONS

Bray, W. E., *Bray's Clinical Laboratory Method,* 6th Ed., CV Mosley Co., 1962, pp. 336–337.
Thompson, R. G. "Technical Methods", J. Clinical Pathology vol. 25, No. 6, Jun. 1972, pp. 546–547.

*Primary Examiner*—Frank W. Lutter
*Assistant Examiner*—Ralph J. Hill
*Attorney, Agent, or Firm*—John S. Roberts, Jr.; Norman J. Latker; Thomas G. Ferris

[57] ABSTRACT

A device and method for the concentration of parasite eggs and larvae consisting of separable upper and lower chambers connected by a mid-piece which incorporates a filter of stainless steel gauze. The sample is emulsified in the upper chamber and is filtered into the lower chamber. Ether is added through the upper chamber and the mid-piece and upper chamber are removed. The lower chamber is shaken and centrifuged, the mid-plug of debris is removed, and the tube is drained and swabbed clean leaving a small sediment containing the parasite eggs and larvae. The sediment is removed by extraction with Lugol's iodine or saline to dilute the sediment.

3 Claims, 8 Drawing Figures

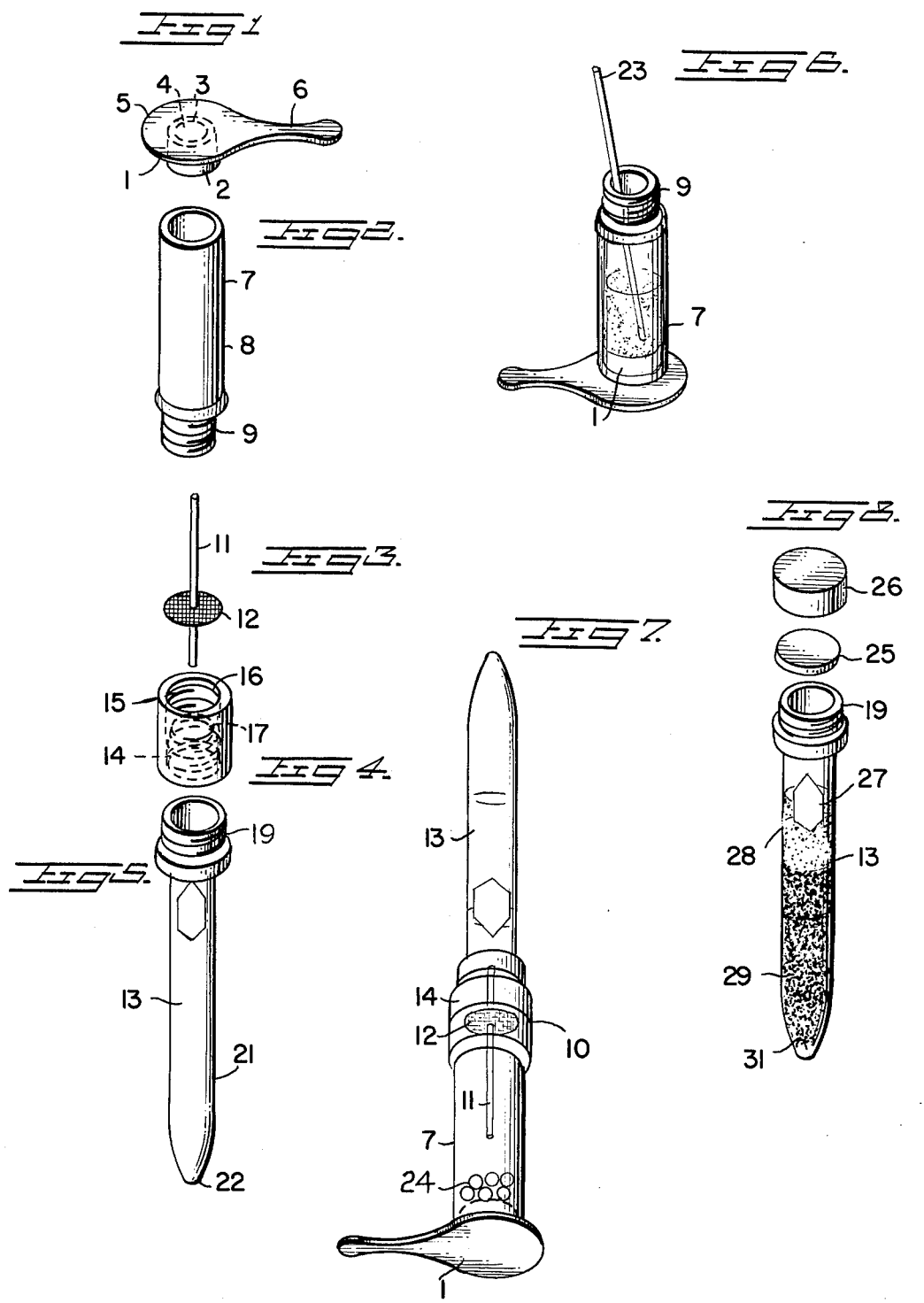

FECALATOR, AN APPARATUS AND METHOD FOR CONCENTRATION OF PARASITE EGGS AND LARVAE

This invention relates to an apparatus and method for the recovery of parasitic eggs and larvae from feces.

The recovery of parasitic eggs and larvae from feces is of major importance in the diagnosis of many diseases. Most of the known methods for the recovery of parasitic eggs and larvae from large volumes of feces are impractical for the routine parasitology laboratory. The conventional formalin-ether method, as disclosed in Laboratory Procedures for the Diagnosis of Intestinal Parasites, 1974, U.S. Department of HEW, PHS Pub. No. 1969, pages 103–105, is time consuming and is esthetically distasteful. The present invention provides an apparatus and method for the recovery of parasitic eggs and larvae from a small feces sample in a clean, efficient and quick manner. The apparatus of the present invention is called a Fecalator and the method of the present invention is called a Fecalator Method.

The Fecalator of the present invention recovers a clear and a small sediment containing parasitic eggs and larvae from a small measured amount of feces sample. Although the entire feces specimen can be processed, however, such a task is time consuming and must be delegated to special laboratories. The Fecalator Method of the present invention approximates the results of large volume methods using a sample as small as one gram of measured feces. Furthermore, the Fecalator Method of the present invention can recover 50-75 times the egg yield of the direct wet mount method whereas the formalin-ether method gave only 2-6 times the egg yield of the direct wet mount method.

SUMMARY OF THE INVENTION

In accordance with the present invention, there is provided a method and apparatus for recovering parasitic eggs and larvae from a feces sample. The apparatus comprises a feces sample cup, an emulsification chamber, a separation chamber, a connector means for joining the emulsification chamber and the separation chamber and a filter means positioned between the chambers. The sample is softened with a solution of formaldehyde and mechanically stirred to homogenize the mixture. Glass beads are added and the mixture is formed into a fine slurry by horizontal shaking of the apparatus. A surfactant may be added to aid release of particularly adhesive eggs such as Ascaris lumbricoides eggs and Strongyloides stercoralis larvae; however, it must be used selectively since a surfactant such as Triton X-100 may destroy such products as protozoan cysts. The apparatus is then shaken vertically to pass the mixture through the filter and ether is added to flush the filter and form a mixture in the separation chamber. The mixture is then agitated and centrifuged and the resultant separation layers are carefully removed to leave a sedentary deposit containing the eggs or larvae.

PRIOR ART

The most pertinent prior art is found in the following patents.

U.S. Pat. No. 3,733,179 of Guehler discloses a four-piece apparatus designed for extraction of blood chemicals. The Fecalator of the present invention is designed totally for the concentration and discovery of parasites in human solid feces samples. The Guehler apparatus could in no way measure a definite feces sample, emulsify this sample, as described in the Fecalator Method, and filter with a proper sized wire gauze centerpiece to allow the parasites in the sample to pass into a container designed as the Fecalator separation chamber in order to remove the debris and concentrate a minute sediment in the tube tip for microscopic examination. The Guehler apparatus could not be used in any way for parasitology work on the feces samples.

U.S. Pat. No. 2,110,237 of Parsons discloses a sediment tester designed for determining sediment in fluid, such as cream. This apparatus would not be able to filter out parasites from a solid debris of human feces. The described filter would do no more than gather the lump mass on the filter. This apparatus could not emulsify a solid feces mass, screen out the microscopic parasites from the debris and collect these in a washed sediment in a tube tip so that a small drop could be examined under a microscope. There would be no part of the apparatus that could be centrifuged for concentration of parasites in human feces.

U.S. Pat. No. 3,888,629 of Bagshawe discloses an apparatus for detection of liquid chemicals. This apparatus would not be suitable for separating helminth eggs and protozoan cysts from human feces. There would be no possibility of measuring or emulsifying a solid feces sample, of correctly separating the parasites through a filter of proper size, and transferring them into a chamber that could be centrifuged in such a manner to separate the mass of amorphous debris and leave the washed parasites in a drop small enough to examine under a microscope. This apparatus could not serve in the capacity the Fecalator is designed for.

U.S. Pat. No. 3,684,455 of Vacirca et al discloses an apparatus for mixing liquids that would be totally inadequate for parasite recovery from human feces. The apparatus does not filter to separate the protozoa from all the amorphous debris. The lower chamber could not be used in the centrifuge for the separation process to separate the sediment for microscopic examination. This device would not perform the test outlined for the Fecalator.

U.S. Pat. No. 3,819,045 of Greenwald discloses a fecal examination apparatus which utilizes a flotation method for recovering parasitic eggs and larvae. This patent does not disclose the apparatus or method of the present invention.

U.S. Pat. No. 3,905,895 of Addis discloses a fecal egg separator which, like Greenwald, utilizes a flotation method for recovering parasitic eggs and larvae. This patent also discloses a centrifugation method for recovering parasitic eggs and larvae; however, this centrifugation method is based upon flotation and is not designed to recover all the parasitic eggs and larvae contained in a feces sample.

The apparatuses by Greenwald and Addis, although both more related to the use that the Fecalator is designed for, do not perform the same way or recover in the same manner. Both are apparatuses devised mainly for the flotation technique and are simpler than the Fecalator apparatus. Neither is designed for washed centrifugal concentration, and therefore heavier eggs, such as Schistosome eggs, are not recovered. This is also true for Strongeloides larvae. There is no provision in either of these devices for utilizing the basic and widely accepted Formalin-Ether Method of concentration relied on by the majority of parasitologists performing tests on human feces. Neither apparatus is designed to collect a total sediment, washed, and centrifuged parasitic collection from an exact human specimen using the standard Formalin-Ether Method of layering and removing fecal debris. The Fecalator, with the unique method featured for emulsifying the material and proper wire filtering, provides for the accepted Standard Formalin-Ether Concentration Method to be performed in the lower chamber, and has been demonstrated to recover all parasitic eggs and larvae that may be in a sample of human feces.

DESCRIPTION OF THE DRAWINGS

FIG. 1 is a perspective view of the feces sample cup.

FIG. 2 is a perspective view of the feces emulsificatipon chamber.

FIG. 3 is a perspective view of the gas passage means and the filter means.

FIG. 4 is a perspective view of the connector means used to join the emulsification chamber and the separation chamber and to hold the gas passage means and the filter means.

FIG. 5 is a perspective view of the separation chamber.

FIG. 6 is a perspective view of the feces sample cup positioned in the feces emulsification chamber and shows a step in the preparation of the feces sample for testing.

FIG. 7 is a perspective view of the assembled Fecalator of the present invention.

FIG. 8 is a perspective view of the separation chamber and shows the contents of the separation chamber after centrifugation.

Referring now to FIGS. 1–5, feces sample cup 1 is a leakproof container and comprises outer wall 2, inner wall 3, bottom 4 and collar 5. Feces sample cup 1 can be provided with handle 6 for ease in handling. Walls 2 and 3 and bottom 4 form a cylindrical closed-bottom container into which the feces sample is placed. The components of feces sample cup 1 are preferably of an integral construction and can be molded from a thermoplastic material such as polyethylene. Emulsification chamber 7 comprises open-ended cylinder 8 which is provided with thread means 9 at its lower extremity. Emulsification chamber 7 can be fabricated from glass or a thermoplastic material such as high density or rigid polyethylene. Outer wall 2 and collar 5 of feces sample cup 1 fit snugly in and around the top of cyclinder 8 of emulsification chamber 1 and form a seal. Gas passage means 11 is a tube, positioned through and secured by filter means 12, provided to permit gas, namely air, to pass from separation chamber 13 to emulsification chamber 7 and to permit emulsion to pass from emulsification chamber 7 through filter means 12 into separation chamber 13. Gas passage means 11 can be fabricated from a thermoplastic material such as polyethylene. A tube with a 0.1 inch outside diameter and 0.06 inch inside diameter has been found suitable for this purpose. Filter means 12 is used to filter emulsion and can be a metal wire gauge or a plastic fiber gauge filter. Best results were obtained using a 30 mesh stainless steel wire gauge filter. Connector means 14 comprises outer wall 15 and inner wall 16 and is provided with inner collar 17 located at the midpoint of inner wall 16 to position filter means 12. Inner wall 16 is provided with thread means 18 which are designed to engage with thread means 9 of emulsification chamber 7 and thread means 19 of separation chamber 13 to connect emulsification chamber 7 and separation chamber 13. Filter means 12 is positioned on inner collar 17 and is held in place by the lower end of emulsification chamber 7. Connector means 14 can be fabricated from a thermoplastic material such as polyethylene and can conveniently be two polyethylene bottle caps joined back to back with a proper size hole through each top. Separation chamber 13 comprises open top cylindrical tube 21 which is provided with thread means 19 at its upper extremity. Cylindrical tube 21 is typically a centrifuge tube and has sides that taper to a closed bottom 22. Separation chamber 13 can be fabricated from glass or a thermoplastic material such as high density or rigid polyethylene. The assembled Fecalator 10 is shown in FIG. 7 in its upright position.

In the following specific examples of the operation of the invention, the compounds identified and defined as follows:

Triton X-100: A Rohm and Haas Company trademark for polyethylene glycol/alkyl aryl ether.

Formalin: An aqueous solution of 37% formaldehyde with sufficient methanol (6–15%) to prevent polymerization.

Lugol's Iodine Solution: A solution containing 5 gm iodine and 10 gm potassium iodide per 100 ml water.

In operation, the cup 1 is filled and leveled with a fecal sample and placed on a horizontal surface. The emulsification chamber F is pressed over the cup 1 (FIG. 6) and formalin solution is added. Using the applicator sticks 23, the specimen is emulsified in the solution so that it is loosened and mixed evenly into a slurry. The suspension is then let stand for about 10 minutes to let the fecal material soften before proceeding. The specimen can also be stored at this stage indefinitely for later processing if covered to prevent evaporation.

Beads 24 (FIG. 7) are then added to the slurry. The beads 24 are preferably made of glass or material having similar density and inert character and are on the order of 4 mm in diameter. It has been found that 5 beads 24 are suitable for the purposes of the invention where particularly adhesive products such as Ascaris lumbricoides eggs and Strongyloides stercoralis larvae are present, it is useful to introduce an oil-in-water surfactant such, for example, as Triton X-100 to the solution at this point. Although the resultant sediment is not as clean and may contain more silt when this surfactant is used, the adhesive quality of these parasites results in their clinging to the debirs, reducing the amount distributed into the sediment. Use of Triton X-100 may be limited because it destroys many protozoan cysts. The addition of Triton X-100 always results in higher egg counts for Ascaris and Toxocara.

The filter means 12 is placed over the top of the emulsification chamber. The connector means 14 is then threaded over the threads 9 on the emulsification chamber 7 to secure the filter means 12. The separation chamber 13 is threaded into the other end of the connector means through the thread means 19 slipped over the chamber to complete the assembly of the Fecalator 10, as shown in FIG. 7, and form a closed container. With the Fecalator 10 held in the position shown in FIG. 7 with a thumb holding securely against the cup 1, the assembly is shaken vigorously in the horizontal direction for about 1 minute. With this agitation, the glass beads 24 actively emulsify the feces-formaldehyde mixture into a smooth, thick slurry. A vortex shaker could also be used for this purpose if desired.

The Fecalator 10 is then inverted and shaken with a firm, vertical up-and-down motion. Under this agitation, the suspension passes into the separation chamber 13 through the filter means 12. In this position the Fecalator 10 is left in a rack (not shown) for about 15 minutes to allow complete draining of the suspension into the separation chamber. Removing the cup 1, any slurry remaining on the filter can be worked through the filter means 12 using an applicator stick 23. There should be little or no debris ramaining in the emulsification chamber F or on the filter means 12 after this step.

Ether is then added into the emulsification chamber F to wash any remaining parasites clinging in the chamber and filter 12 into the separation chamber 13.

The connector means 14, filter 12, beads 24, and the emulsification chamber F are then removed from the separation chamber 13 and a cap 26 and gasket 25 (FIG. 8) are threaded onto the separation chamber 13. Gasket 25 can be fabricated from an elastomeric material such as silicone rubber and cap 26 can be fabricated from a thermoplastic material such as polyethylene. The formaldehyde-ether mixture is then shaken vigorously for 30 seconds, inverting the chamber 13 several times during shaking. The cap 24, gasket 25, and thread means 19 are then removed and the chamber 13 is then placed in a centrifuge (not shown) and centrifuged. After centrifugation, three layers are present in centrifugation chamber 13, namely, top ether layer 27, large middle layer or plug 28 containing feces solids, and a clear lower liquid level 29 with packed sediment 31 in the bottom.

By holding the chamber 13 nearly horizontal, the ether layer 27 can be poured off and the plug 28 rimmed with an applicator 23 and removed with an outward thrust. The fluid layer 29 will then run out, leaving the sediment 31 undisturbed. The walls of the chamber 13 should then be wiped with one or more loosely wrapped cotton swabs to remove adherent residual material so that the inner surface is cleaned to within one half inch of the sediment 31. Care must be taken not to hold the tube upright before the fecal solids and supernatant have been completely removed from the chamber 13 and the walls completely cleaned.

Using a Pasteur pipette with bulb attached, gently mix the sediment 31 with a drop or two of Lugol's iodine, or saline, if preferred, and draw the material into the pipette. The iodine dilutes the small sediment mass and stains cysts and eggs. Saline may be used if preferred. If the entire sediment is examined, which is necessary if counting is done or if eggs are extremely rare, it may be mounted on a 3×2 inch glass slide in one or two mounts, using respectively, two 22×40 mm coverslips or one 23×50 mm coverslip. Examination is performed most accurately by methodically surveying the entire coverslip area with the 10 x objective lens of the microscope.

PREFERRED EMBODIMENTS

The following examples illustrate the practice of the present invention and a mode of utilizing the present invention.

EXAMPLE 1

1 gram of feces sample was homogenized in 9.0 ml of a 10% aqueous formalin solution. 0.3 ml of a 20% aqueous solution of Triton X-100 was added to the slurry and the mixture was emulsified and filtered as described above.

3 ml of ether was mixed with the filtrate and the solution was centrifuged at 1500 rpm (310 Relative Centrifugal Force) for three minutes.

The ether-formalin solution ratio used in this example yielded results at least as good as those of Example 2, following, and the ratio is consistent with that which is standard in the industry.

EXAMPLE 2

The procedure of Example 1 was repeated with 5.5 ml of formalin and 5 ml of ether instead of the quantities used in Example 1.

EXAMPLE 3

The same procedure used for testing one gram feces samples in Example 2 was repeated with the exception that Triton X-100 was not added to the feces-formalin slurry. Samples 1–14 were tested in accordance with the above procedure. Results of this example are contained in Table I.

EXAMPLE 4

Samples 1–14 were tested using the conventional formalin-ether method. Results of this example are contained in Table I.

EXAMPLE 5 samples 1–14 were tested using the direct wet mount method. Results of this example are contained in Table I.

The method of the present invention recovered 50 to 75 times more parasitic eggs than the direct wet mount method. The conventional formalin-ether method averaged 2 to 6 times more recovery than the direct wet mount method. For example, Schistosoma mansoni, Samples 1 and 2 yielded 3 and 2 eggs by the direct wet mount method, 18 and 3 eggs by the formalin-ether method, and 155 and 136 eggs by the method of the present invention. Strongyloides stercoralis larvae were not recovered by the direct wet mount method from either Sample 4 of 5. The formalin-ether method yielded one larva in Sample 5 while the method of the present invention yielded 14 larvae and 5 larvae, respectively, in the two different samples. Hookworms eggs recovered in Sample 6 numbered 6 eggs by the direct wet mount method, 118 eggs by the formalin-ether method, and 140 by the method of the present invention. Ascaris lumoricoides eggs were counted in Sample 8 and 45 eggs were recovered by the direct wet mount method, while only 9 eggs were recovered by the formalin-ether method. The method of the present invention yielded 3170 eggs from a gram of Sample 8 when Triton X-100 was used. Trichuris trichiura eggs demonstrated the same recovery pattern. In Sample 9 no eggs were found by the direct wet mount method and only 2 eggs by the formalin-ether method. The method of the present invention recovered 18 eggs. In Samples 9 and 10, the direct wet mount method recovered only 2 eggs from Sample 10, while the method of the present invention recovered 18 eggs from Sample 9 and 198 from Sample 10. Sample 11 demonstrates the advantage of using Triton X-100 in the method of the present invention. 9000 eggs were recovered using Triton X-100, while only 1120 eggs were recovered without using Triton X-100. In Sample 3, 937 Schistasoma mansoni eggs were recovered using Triton X-100, while only 74 eggs were recovered using no Triton X-100. In Sample 7, 781 hookworm eggs were recovered using Triton X-100 while only 117 eggs were recovered using no Triton X-100.

TABLE I

| Fecal Sample Containing Parasitic Eggs and Larvae | Example 2 Method of the Present Invention Using Triton X-100 5/5.5 ml Ether/Formalin | Example 3 Method of the Present Invention Without Triton X-100 | Example 4 Formalin-Ether Method | Example 5 Direct Wet Mount Method* |
|---|---|---|---|---|
| Sample 1 Schistosoma Mansoni eggs | 155 eggs | 234 eggs | 18 eggs | 3 eggs |
| Sample 2 Schistosoma Mansoni eggs | 136 eggs | 54 eggs | 3 eggs | 2 eggs |
| Sample 3 Schistosoma Mansoni eggs | 937 eggs | 74 eggs | — | 3 eggs |
| Sample 4 Strongyloides Stercoradis larvae | 14 larvae | — | 0 larvae | 0 larvae |
| Sample 5 Strongyloides Stercoradis larvae | 5 larvae | — | 1 larvae | 0 larvae |
| Sample 6 Hookworm eggs | 140 eggs | — | 118 eggs | 6 eggs |
| Sample 7 Hookworm eggs | 781 eggs | 117 eggs | — | 3 eggs |
| Sample 8 Ascaris lumbricoides eggs | 3170 eggs | — | 9 eggs | 45 eggs |
| Sample 9 Trichuris trichiura eggs | 9 eggs | 18 eggs | 2 eggs | 0 eggs |
| Sample 10 Trichuris trichiura eggs | 198 eggs | 80 eggs | — | 2 eggs |
| Sample 11 Trichuris trichiura eggs | 9000 eggs | 1120 eggs | — | 61 eggs |
| Sample 12 Trichuris trichiura eggs | 123 eggs | 59 eggs | — | 1 egg |
| Sample 13 Ascaris lumbricoides eggs | 116 eggs | 26 eggs | — | 6 eggs |
| Sample 14 Ascaris lumbricoides eggs | 1787 eggs | 15 eggs | — | 30 eggs |

*The wet mount method is approximately 2 mg of fecal material in normal saline mounted on a glass slide and, using a 22 × 44 mm coverslip, examined under microscope.

The above description and examples are intended to be exemplary of a teaching in accordance with the invention to aid those skilled in the art in the practice thereof.

What is new and desired to be protected by Letters Patent of the United States is:

1. A method of recovering parasitic eggs and larvae from a measured sample of feces which comprises:
   (a) softening and homogenizing said sample in a tube having an open end utilizing formaldehyde adding an oil-in-water surfactant with mechanical stirring agitation;
   (b) closing said open end with a filter means and a separation chamber;
   (c) agitating in a horizontal direction in said tube;
   (d) inverting and shaking said tube vertically to filter said sample through said filter into said separation chamber and adding ether to complete the filtration to produce a formalin-ether mixture with said sample;
   (e) reagitating the formalin-ether mixture and said sample; and
   (f) centifuging said mixture and sample to produce three layers, namely, (1) top layer containing ether, (2) intermediate layer containing fecal solids, and (3) bottom layer containing clear fluid and packed sediment with said eggs.

2. The method according to claim 1 wherein said surfactant comprises 20% Triton X-100 in water.

3. An apparatus for recovering parasitic eggs and larvae from a fecal sample comprising:
   (a) cup for measuring a predetermined quantity of fecus;
   (b) an open ended tube adapted to sealingly receive said cup in one end thereof to form an emulsification chamber therewith;
   (c) filter means adapted to cover the other end of said tube to filter the contents, said filter means therefore further including a coaxial tube to provide for passage of gas driving filtration;
   (d) a tube forming a separating chamber adapted to fit over the open end of said emulsification chamber to receive the filtered contents thereof; and
   (e) annular collar means to releasably connect said emulsification and separating chambers to form a closed container therewith.

* * * * *

UNITED STATES PATENT OFFICE
CERTIFICATE OF CORRECTION

Patent No. 4,081,356          Dated March 28, 1978

Inventor(s) Willadene S. Zierdt

It is certified that error appears in the above-identified patent and that said Letters Patent are hereby corrected as shown below:

Column 4, line 49, "debirs" should be --debris--

Column 5, line 10, "ramaining" should be --remaining--

Column 8, line 56, "driving" should be --during--

Signed and Sealed this

Fifth Day of September 1978

[SEAL]

Attest:

RUTH C. MASON
*Attesting Officer*

DONALD W. BANNER
*Commissioner of Patents and Trademarks*